United States Patent
Welliver et al.

(10) Patent No.: US 11,123,502 B2
(45) Date of Patent: Sep. 21, 2021

(54) VAPORIZER CARTRIDGE SYSTEM

(71) Applicant: JJ & J Industries LLC, Sammamish, WA (US)

(72) Inventors: John Joseph Welliver, Sammamish, WA (US); Jeffrey Edward Carlson, Highland, CA (US)

(73) Assignee: JJ & J Industries LLC, Sammamish, WA (US)

( * ) Notice: Subject to any disclaimer, the term of this patent is extended or adjusted under 35 U.S.C. 154(b) by 0 days.

(21) Appl. No.: 16/586,721

(22) Filed: Sep. 27, 2019

(65) Prior Publication Data

US 2020/0100543 A1    Apr. 2, 2020

Related U.S. Application Data

(60) Provisional application No. 62/737,722, filed on Sep. 27, 2018.

(51) Int. Cl.
| | |
|---|---|
| *A24F 40/10* | (2020.01) |
| *A24F 40/46* | (2020.01) |
| *A61M 11/04* | (2006.01) |
| *A24B 15/167* | (2020.01) |

(52) U.S. Cl.
CPC ........... *A61M 11/042* (2014.02); *A24F 40/10* (2020.01); *A24F 40/46* (2020.01); *A24B 15/167* (2016.11); *A61M 2205/8206* (2013.01)

(58) Field of Classification Search
CPC ........ A24F 47/008; A24F 40/10; A24F 40/46; A61M 11/042
USPC .......................................................... 131/328
See application file for complete search history.

(56) References Cited

U.S. PATENT DOCUMENTS

| | | | | |
|---|---|---|---|---|
| 8,689,805 | B2 * | 4/2014 | Hon | A24F 47/008 131/273 |
| 9,440,035 | B2 * | 9/2016 | Chung | A61M 15/002 |
| 9,877,515 | B2 * | 1/2018 | Liu | A24F 47/008 |
| 10,791,762 | B2 * | 10/2020 | Liu | A24F 40/46 |
| 2013/0087160 | A1 * | 4/2013 | Gherghe | A24F 1/00 131/329 |
| 2014/0041655 | A1 | 2/2014 | Barron et al. | |

(Continued)

FOREIGN PATENT DOCUMENTS

| | | | |
|---|---|---|---|
| KR | 200470845 Y1 | 1/2014 | |
| WO | WO-2016109932 A1 * | 7/2016 | ............. A24F 47/00 |

OTHER PUBLICATIONS

Machine Translation of WO 2016109932 (Year: 2016).*

(Continued)

*Primary Examiner* — Eric Yaary
*Assistant Examiner* — Russell E Sparks
(74) *Attorney, Agent, or Firm* — Rowan Tels LLC

(57) ABSTRACT

A vaporizer cartridge system includes a vaporizer assembly containing a heating element, a mouthpiece that is selectively attachable with the vaporizer assembly, a battery assembly that is selectively attachable with the vaporizer assembly, and a cartridge configured to store liquid in a reservoir, the cartridge being selectively attachable with the vaporizer assembly such that liquid stored within the reservoir is in fluid communication with the vaporizer assembly. The vaporizer cartridge system is configured such that when the cartridge and the mouthpiece are attached to the vaporizer assembly, the cartridge fits within the mouthpiece.

14 Claims, 16 Drawing Sheets

(56) References Cited

U.S. PATENT DOCUMENTS

| | | | |
|---|---|---|---|
| 2014/0290676 A1* | 10/2014 | Liu | A24F 47/008 |
| | | | 131/329 |
| 2015/0020829 A1 | 1/2015 | Li | |
| 2016/0128387 A1* | 5/2016 | Chen | A24F 47/008 |
| | | | 392/395 |
| 2016/0219937 A1* | 8/2016 | Rado | A24F 40/40 |
| 2017/0035115 A1 | 2/2017 | Monsees et al. | |
| 2017/0127722 A1* | 5/2017 | Davis | H05B 6/108 |
| 2018/0303166 A1* | 10/2018 | Qiu | F16K 24/04 |
| 2019/0053544 A1* | 2/2019 | Yamada | A61M 11/042 |
| 2020/0113235 A1* | 4/2020 | Fernando | A24F 1/30 |

OTHER PUBLICATIONS

International Search Report for PCT Application PCT/US2019/053641, dated Dec. 3, 2019.

International Written Opinion for PCT Application PCT/US2019/053641, dated Dec. 3, 2019.

* cited by examiner

VAPORIZER CARTRIDGE SYSTEM

CROSS-REFERENCE TO RELATED APPLICATIONS

This application claims the benefit of U.S. provisional patent application Ser. No. 62/737,722, filed on Sep. 27, 2018, the contents of which are incorporated herein by reference in their entirety.

BACKGROUND

The vaping industry has progressed rapidly over a relatively short period of time. Not least due to this popularity, vaping devices have proliferated; however, in many respects this popularity has diminished the quality of the vaping devices themselves. The challenges of creating a device with high quality, detachable and replaceable parts, e.g., where some parts may be retained and others easily and simply swapped for a newer version, extend to the composition of the device.

Many devices tend to be both of comparatively high cost and also disposable, e.g., when a user consumes the vaporizing liquid, he simply throws the entire assembly away. Similar behaviors may apply to other parts, such as but not limited to, the cartridge holding the vaporizing liquid, the heating element, the battery, and the various bushings and gaskets holding the assembly together.

Therefore, there exists a need for a renewable vaporizer cartridge system, fitted together with selectively detachable parts, of which many of the parts may be retained when others wear out or are consumed.

BRIEF SUMMARY

The disclosure describes a vaporizer cartridge system. In one embodiment a vaporizer cartridge system is disclosed comprising a vaporizer assembly comprising a vaporizer body, a heating element selectively attachable with the vaporizer body, an insulator bushing selectively attachable with the vaporizer body, a center conductor selectively attachable with the insulator bushing and the vaporizer body, a lock ring located between grooves in the vaporizer body and grooves in the center conductor, a first seal between the vaporizer body and a reservoir, and a second seal between the vaporizer body and the heating element. The vaporizer cartridge system additionally comprises a mouthpiece selectively attachable with the vaporizer assembly, a battery assembly that is selectively attachable with the vaporizer assembly, and a cartridge configured to store liquid in a reservoir, the cartridge being selectively attachable with the vaporizer assembly such that liquid stored within the reservoir is in fluid communication with the vaporizer assembly, wherein the vaporizer cartridge system is configured such that when the cartridge and the mouthpiece are attached to the vaporizer assembly, the cartridge fits within the mouthpiece.

In another embodiment, a method of using a vaporizer cartridge system is disclosed, the method comprising providing a vaporizer cartridge system, including a vaporizer assembly comprising a vaporizer body, a heating element selectively attachable with the vaporizer body, an insulator bushing selectively attachable with the vaporizer body, a center conductor selectively attachable with the insulator bushing and the vaporizer body, a lock ring located between grooves in the vaporizer body and grooves in the center conductor, a first seal between the vaporizer body and a reservoir, and a second seal between the vaporizer body and the heating element. The vaporizer cartridge system additionally comprises providing a mouthpiece that is selectively attachable with the vaporizer assembly, a battery assembly that is selectively attachable with the vaporizer assembly, and a cartridge configured to store liquid in a reservoir, the cartridge being selectively attachable with the vaporizer assembly such that liquid stored within the reservoir is in fluid communication with the vaporizer assembly, wherein the vaporizer cartridge system is configured such that when the cartridge and the mouthpiece are attached to the vaporizer assembly, the cartridge fits within the mouthpiece. The method of using a vaporizer cartridge system additionally comprises drawing fresh air into the vaporizer cartridge system by creating a suction on an end of the mouthpiece and partially vaporizing at least a portion of the liquid using the heating element.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
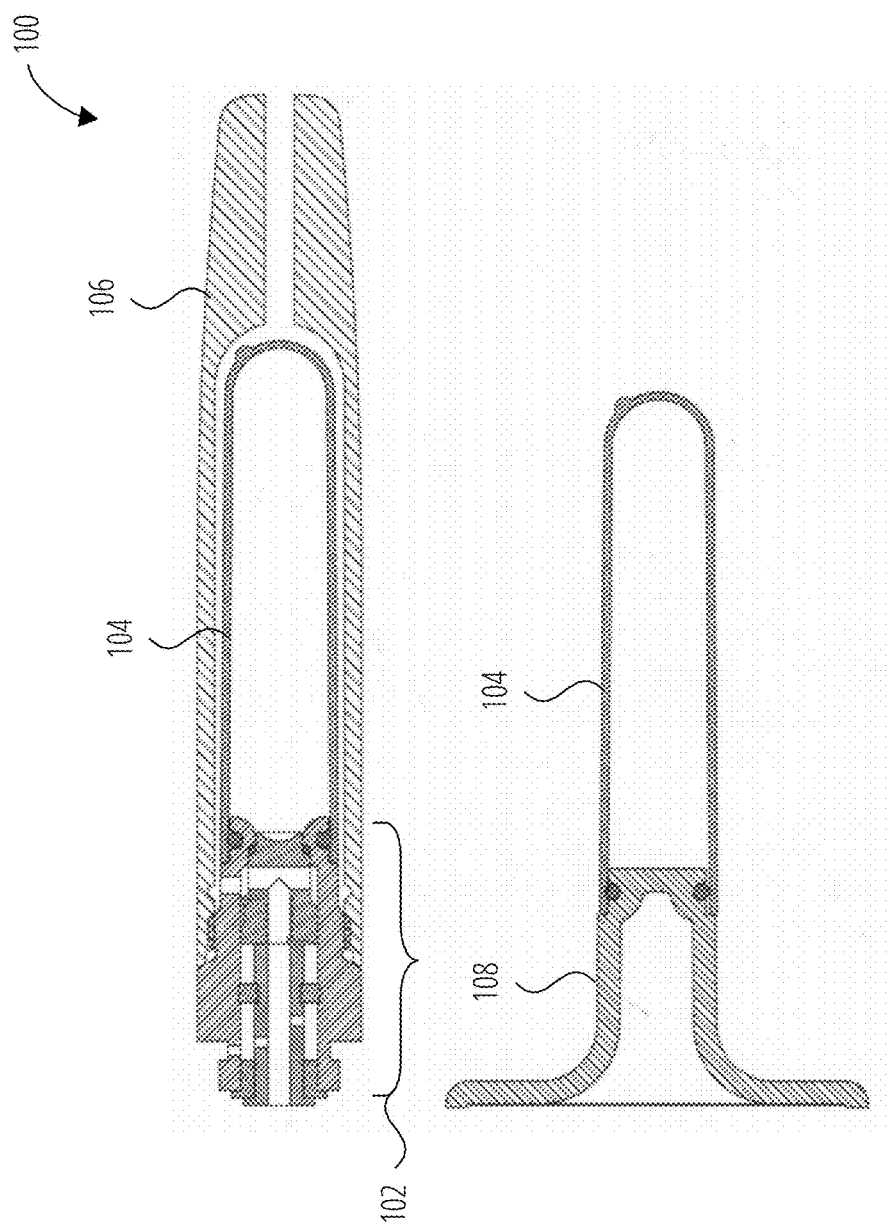
FIG. 1 illustrates a side section view of a representative vaporizer cartridge system 100 in accordance with one embodiment.

"Battery assembly" refers to a selectively attachable component of the vaporizer assembly including a battery unit and battery cover.

"Battery cover" refers to a physical covering for the battery. Both the battery and battery cover are part of the battery assembly.

"Cap" refers to a removable covering, fitted onto the end of the cartridge to plug the outlet of the cartridge to prevent the exit of liquid.

"Cartridge" refers to a selectively attachable component of the vaporizer assembly, fitting within the mouthpiece, containing vaporable liquid.

"Cartridge reservoir" refers to the interior, liquid-storage cavity within the cartridge.

"Center conductor" refers to an electrically conducting selectively attachable component of the vaporizer assembly.

"Center conductor cavity" refers to a spacing extending through the center of the center conductor and providing a fluid connection between the battery assembly, the plurality of air holes in the center conductor, and the heating element.

"Exhaust air cavity" refers to a pocket containing air between the heating element and the vaporizer body.

"First center conductor surface" refers to a physical area on the center conductor contacting a positive contact on the battery assembly.

"First o-ring" refers to a flexible gasket-like component forming at least in part the first seal between the vaporizer body and the cartridge.

"First seal" refers to a sealed connection.

"Fresh air intake holes" refers to openings within the vaporizer body allowing for an exterior air source to flow into the vaporizer assembly.

"Heating coil" refers to a device used to heat the heating element.

"Heating element" refers to a selectively detachable component of the vaporizer assembly that provides heat to vaporize liquid and transfer liquid from a reservoir to the heating coil.

"Heating element cavity" refers to a space within the heating element body in fluid communication with a plurality of fresh air intake holes in the vaporizer body.

"Heating element exhaust passage" refers to a passageway through the heating element body in fluid communication with the heating element cavity.

"Insulator bushing" refers to a selectively attachable component electrically isolating certain surfaces of the vaporizer assembly.

"Liquid" refers to a vaporizable fluid substance located within the cartridge reservoir.

"Liquid contact surface" refers to an area of the heating element in contact with the liquid inside the reservoir.

"Lock ring" refers to a component located between the groove in the center conductor and the groove in the vaporizer body.

"Mouthpiece" refers to a selectively attachable component of the vaporizer assembly through which a user draws vapor created by liquid being exposed to a heating element.

"Negative heating coil lead" refers to an electrical lead on the heating coil, in contact with the vaporizer body.

"Plurality of air holes" refers to multiple opening through the wall of the center conductor, in fluid communication with the center conductor cavity and the cavity between the fresh air intake holes, the center conductor, the insulator bushing, and the lock ring.

"Plurality of exhaust holes" refers to multiple openings in the vaporizer body in fluid communication with the exhaust air cavity and the mouthpiece.

"Plurality of fresh air intake holes" refers to multiple openings in the vaporizer body in fluid communication with the air passage in the center conductor cavity.

"Positive heating coil lead" refers to an electrical lead on the heating coil, in contact with the center conductor.

"Reservoir" refers to the interior space within the cartridge comprising a liquid.

"Second center conductor surface" refers to a physical area on the center conductor contacting a heating element.

"Second o-ring" refers to a flexible gasket-like component forming at least in part the second seal between the vaporizer body and the heating element.

"Second seal" refers to a sealed connection.

"Third center conductor surface" refers to a physical area on the center conductor contacting an insulator bushing.

"Vaporizer" refers to a component of the vaporizer assembly responsible for creating vapor by exposing a vaporable liquid to a heating element.

"Vaporizer assembly" refers to a collection of vaporizing components, comprising at least one of a vaporizer body, heating element, insulator bushing, center conductor, lock ring, first seal, and second seal.

"Vaporizer body" refers to the central physical component of the vaporizer assembly, connecting to the center conductor via a lock ring, the insulator bushing, the heating element and the cartridge.

"Vaporizer cartridge system" refers to a system including a selectively attachable vaporizer assembly, a selectively attachable battery assembly, a selectively attachable mouthpiece, and a selectively attachable cartridge.

To meet the challenges of a flexible vaping device with selectively detachable and attachable components, a vaporizer cartridge system is disclosed. The main components of the device fit together via threads, bushings, lock rings, seals and contacts. Therefore, common replaceable vaping device parts such as a battery, mouthpiece, liquid-storing cartridge, and cartridge cap may be easily snapped loose or unscrewed from connecting parts and replaced without disposing of the entire assembly. The user may partially disassemble the vaporizer cartridge system, replace a replaceable part, and then reassemble the system. In various embodiments, the detachability of these components may not sacrifice the overall device performance, such as delivering vapor to users in a way users have come to expect. The ability to replace parts of a vaporizer cartridge system may allow for greater customization of an individual's vaping device and potentially reduced overall cost of the device since a user may not need to purchase an entirely new device when the vaporizing liquid is depleted, or when any individual component, such as a heating element or battery, wears out, or becomes obsolete.

Referring to FIG. 1, a side section view of a representative vaporizer cartridge system 100 is illustrated according to an embodiment. A representative vaporizer cartridge system includes a vaporizer assembly 102, a cartridge 104, and a mouthpiece 106 in a connected assembly. The vaporizer assembly 102 may selectively attach to a battery, and the cartridge 104 and mouthpiece 106 may selectively attach to the vaporizer assembly 102. The cartridge 104 includes a reservoir configured to store a liquid (e.g., vaping liquid) and may be selectively attached to the vaporizer assembly 102 such that the reservoir is in fluid communication with the vaporizer assembly 102. The cartridge 104 may be removed from the vaporizer assembly 102 when the oil is consumed.

During storage, shipment, or when removed from the vaporizer assembly 102, an opening of the cartridge 104 may be closed with a removable device, such as the cap 108 as shown, to prevent spilling.

The liquid contained in the cartridge may be any vaporizable vaping fluid a user would use in a vaping device, including but not limited to oils and other fluids creating vapors or aerosols upon contact with heat or a heating element.

Figure 2:
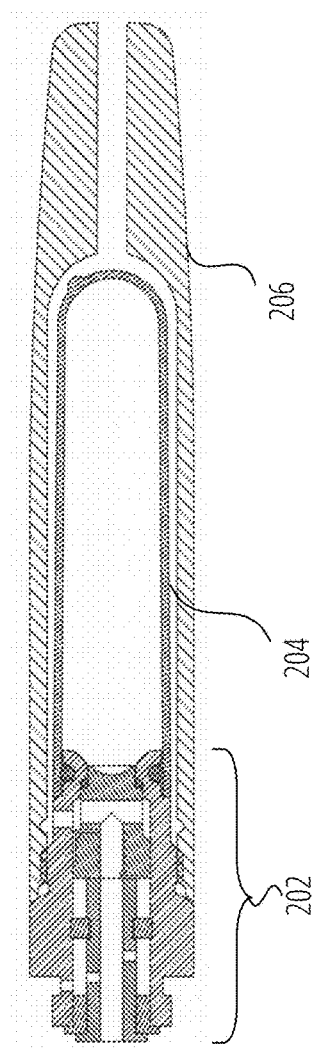
FIG. 2 illustrates a side section view of the vaporizer cartridge system 200 in accordance with one embodiment.

Referring to FIG. 2, a side section view of the vaporizer cartridge system 200 illustrates that the mouthpiece 206 may attach to the vaporizer assembly 202 over the cartridge 204, leaving a vapor passageway between an external surface of the cartridge 204 and an internal surface of the mouthpiece 206.

The mouthpiece of the vaporizer assembly may be of any material that would function in this service. In exemplary embodiments, the material may be non-allergic to human contact, able to withstand contact with heat, vapors and human saliva, e.g., when a user draws vapor from it, and of sufficient pliancy to have threads cut into it to screw onto another section of the vaporizer assembly. In other embodiments, the mouthpiece may have a snap connection or a ¼ turn connection. Most plastics and non-allergic metals may suffice.

The cartridge may be of any non-reactive material able to store oils and other liquids capable of vaporizing when in contact with heat or a heating element. The cartridge may also be sufficiently pliable to have grooves cut into its lip or open end to allow a cap or similar enclosure to prevent spillage from the cartridge outlet.

Figure 3:
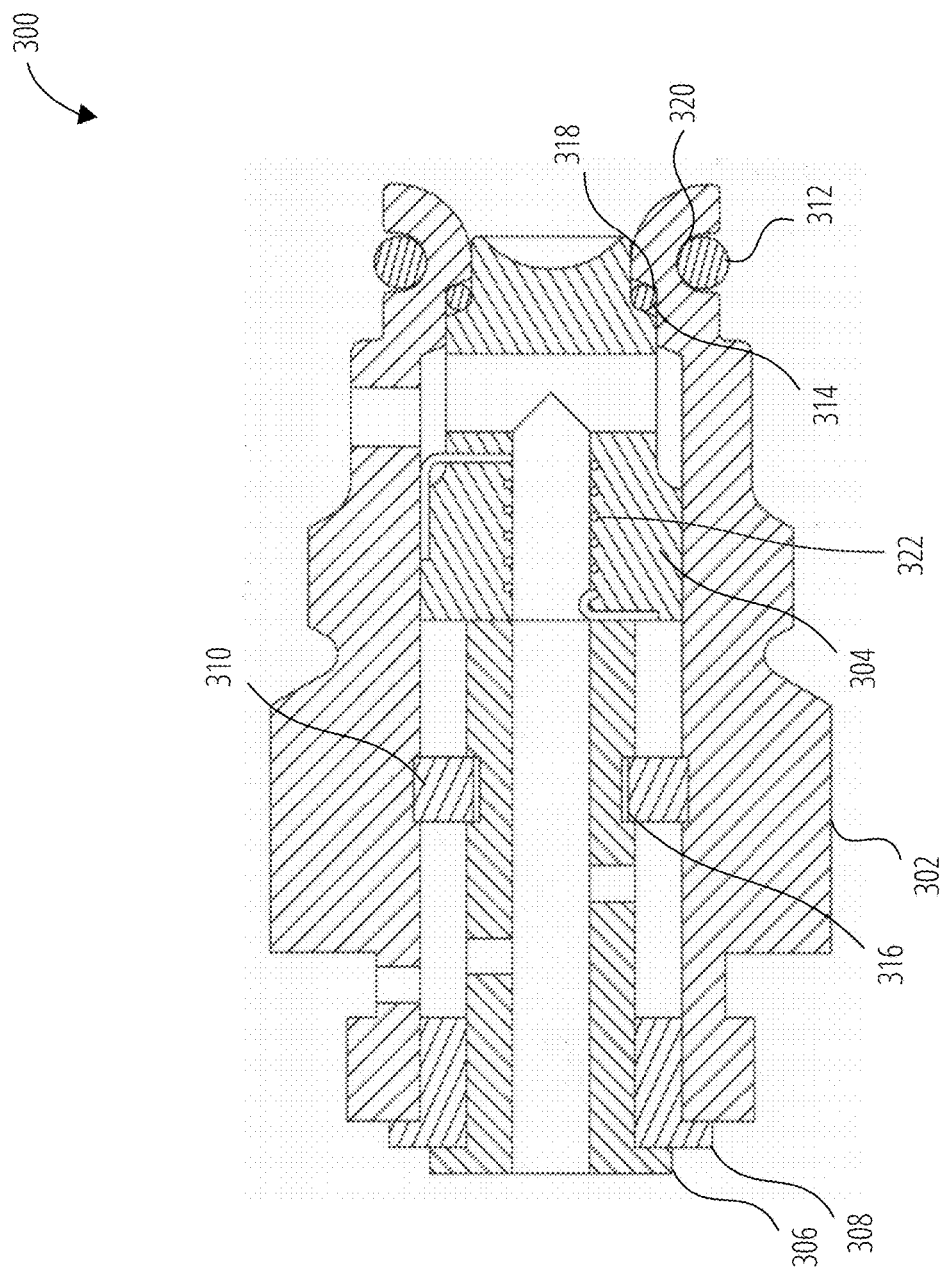
FIG. 3 illustrates a side section view of a vaporizer assembly 300 in accordance with one embodiment.

FIG. 3 shows a side section view of a vaporizer assembly 300 in an assembled state according to an embodiment. The vaporizer assembly includes a vaporizer body 302, which is the main body of the vaporizer assembly that all of the other vaporizer assembly parts are installed into or onto. A heating element 304 absorbs the liquid from the cartridge reservoir, transfers the liquid from the cartridge to the heating coil 322, causes the liquid medium to vaporize on the heating coil, and provides a path for the vapor to be transferred away from the heating coil. A center conductor 306 completes the circuit from the positive contact on the battery to the heating element 304 coil, provides a pathway for fresh air to reach the heating coil, and provides part of the locking mechanism, which holds the parts within the vaporizer assembly together. An insulator bushing 308 prevents electrical shorting between the positive and negative circuit within the vaporizer assembly, and creates an airtight seal to direct the flow of fresh air through the correct passages within the vaporizer assembly. A lock ring 310 fits with its lock ring grooves 316 between grooves in the vaporizer body 302 and the center conductor 306 to lock the parts of the vaporizer assembly together and to create an airtight seal to direct the flow of fresh air through the correct passages within the vaporizer assembly. In one embodiment, a first o-ring 312 creates a first seal 320 between the vaporizer body 302 and the cartridge reservoir, while a second o-ring 314 creates a second seal 318 between the vaporizer body 302 and the ceramic heating element 304.

The vaporizer body may comprise a non-reactive material, typically but not necessarily metallic. In an embodiment, the vaporizer body is able to withstand temperatures of approximately 315 to 450 degrees Fahrenheit (157 to 232 degrees Celsius), typically from the heating element and/or heating coil operating inside.

The heating element for the vaporizer assembly may be able to withstand electrically stimulated temperature of up to 450 degrees Fahrenheit (232 degrees Celsius). The heating element may be of a porous, high-tempered material (e.g., ceramic) for the purpose of absorbing a vaporizing liquid. The porous material may also be of varying porosity to control the flow of liquid within it and to prevent leakage of the liquid into unwanted areas (e.g., more porous to encourage the flow of liquid and less porous to discourage the flow of liquid). The heating element may also be coated in certain areas to prevent leakage, or to control the absorption of liquid.

The center conductor may be made of an electrically conductive, non-reactive tempered material able to be punctured and carved in a variety of ways, including but not limited to hole drilling, thread carving and boring (e.g., to create an air passage). A metallic material may typically suffice for creating the center conductor in a machining, molding, die-casting or similar forming process known to those skilled in the art.

The insulator bushing fitting onto the center conductor may be made of a non-electrically conductive, non-reactive material able to be cylindrically or otherwise bored in a size-customized manner. A plastic or ceramic material may typically suffice for creating the insulator bushing in a machining, molding, die-casting or similar forming process known to those skilled in the art.

The lock ring located within the grooves between the vaporizer body and center conductor serves a locking purpose and a gasket-like purpose and may be made of high-temperature plastic, silicone or similar material for forming an effective seal next to or between two components.

The O-rings (e.g., first o-ring and second o-ring) may be made of rubber, or, more specifically, elastic polymers, or elastomers. These polymers are cured, often through vulcanization, resulting in a strong, durable and more elastic rubber. Other O-ring materials may include PTFE, Nitrile (Buna), Neoprene, EPDM Rubber and Fluorocarbon (Viton). Silicone and Kalrez® O-ring materials are also widely used, especially in high temperature applications such as this disclosure.

Figure 4:
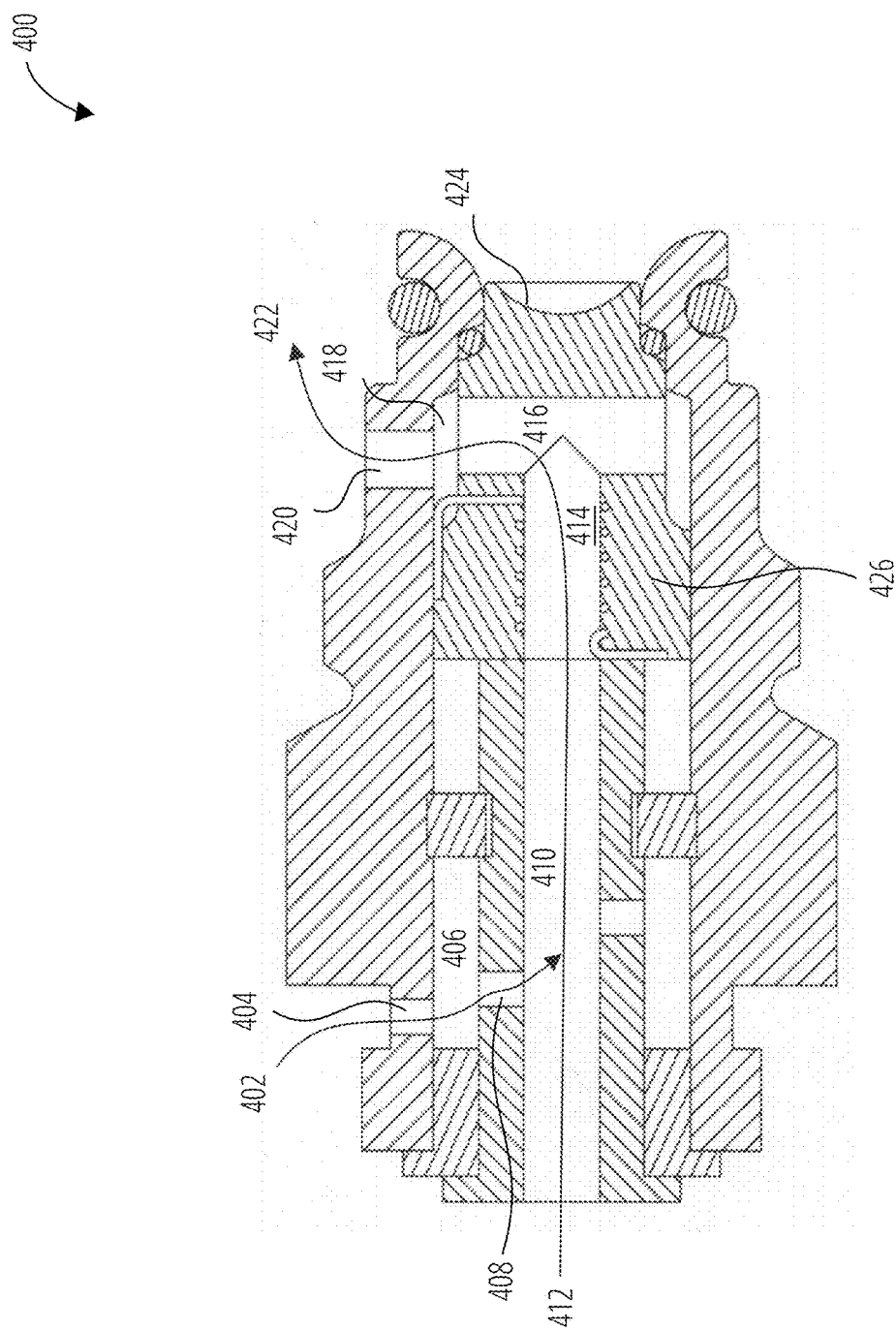
FIG. 4 illustrates a side section view showing fluid flow through the vaporizer assembly 400 in accordance with one embodiment.

FIG. 4, a side section view showing fluid flow through the vaporizer assembly 400, illustrates the path of flow of air and liquid medium throughout the vaporizer assembly. Fresh air flow 402 shows the path of fresh air entering the vaporizer body. One of the fresh air intake holes 404 indicates the air intake hole in the vaporizer body. A cavity 406 indicates such a space between the vaporizer body, the center conductor, the insulator bushing, the lock ring. A plurality of air holes 408 indicates air holes in the center conductor. A center conductor cavity 410 indicates a hole that extends all the way through the centerline of the center conductor. Air combines in this passageway from the battery and from outside the vaporizer assembly at the fresh air flow 402 and is transferred to the heating element cavity 414 by way of the heating element 426.

A battery assembly air source 412 indicates where air enters the vaporizer assembly from the battery assembly. The purpose of this is so that suction from the mouthpiece can actuate a battery that has a suction switch mechanism. Fresh air enters the heating element cavity 414 where the air picks up vaporized liquid and passes through to the heating element exhaust passage 416. An exhaust air cavity 418 indicates a cavity between the ceramic heating element 426 and the vaporizer body where air and vapor can escape through a plurality of exhaust holes 420 in the vaporizer body. A flow path to exterior 422 indicates a flow path when the mouthpiece and cartridge are attached to the vaporizer assembly. The air travels in this direction via the flow path between the mouthpiece and the cartridge where it exits through the air hole in the mouthpiece. A surface 424 represents the surface of the heating element 426 material that comes in contact with the liquid inside the cartridge reservoir. The liquid may permeate (i.e., soak) into the surface. This surface may be curved as shown, or flat. It is shown curved to create more surface area for better absorption of the liquid medium.

In an embodiment, the intake and other holes (i.e., fresh air intake holes, plurality of air holes, plurality of fresh air intake holes) serving various purposes described above may be bored into the respective components within the vaporizer assembly, e.g., the vaporizer body and center conductor, by use of a commercial or other drilling device known to those skilled in the art for forming passages into machined, die-cast or otherwise molded components.

Figure 5:
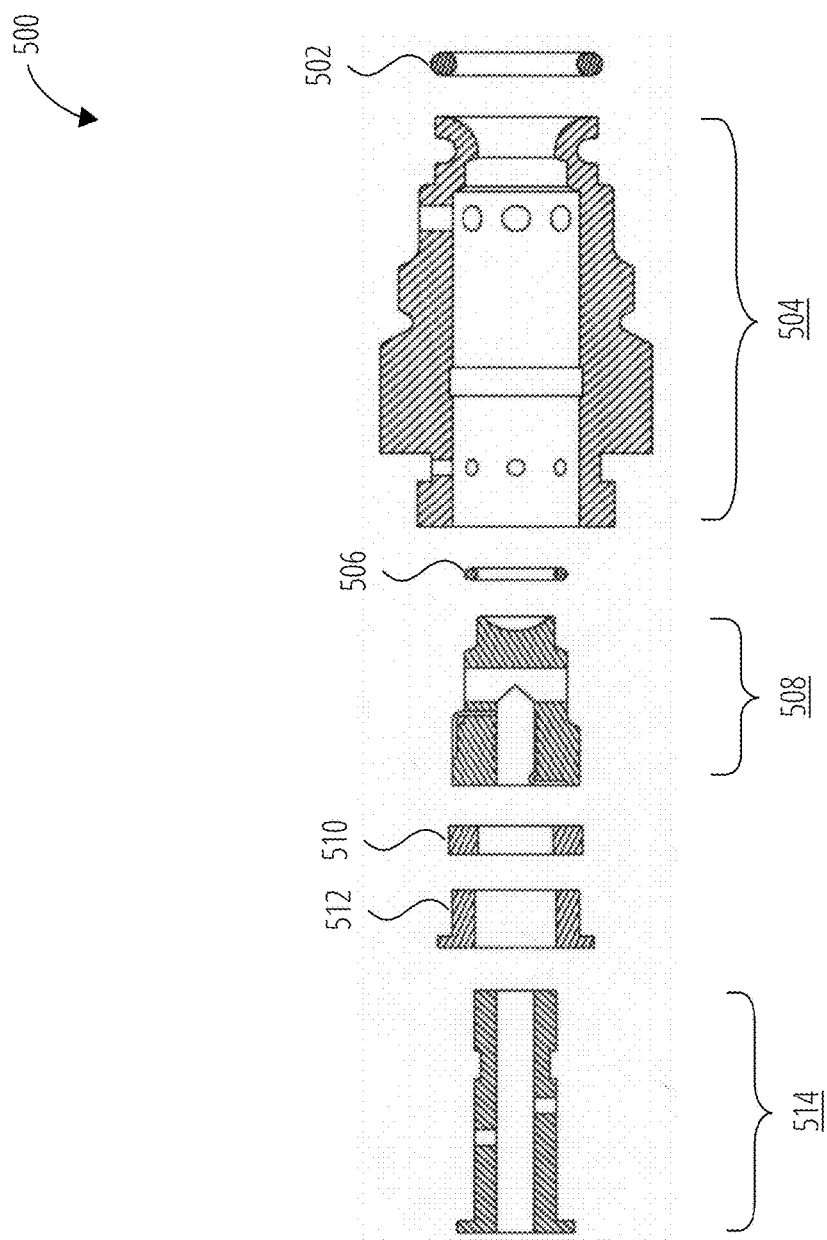
FIG. 5 illustrates an exploded side section view of the vaporizer assembly 500 in accordance with one embodiment.

FIG. 5 illustrates an exploded side section view of the vaporizer assembly 500, the structure of the vaporizer body 504 that enables rapid assembly and disassembly. The first o-ring 502, vaporizer body 504, second o-ring 506, heating element 508, lock ring 510, insulator bushing 512, and center conductor 514 assemble concentrically and in series, to for example, facilitate serviceability.

Figure 6:
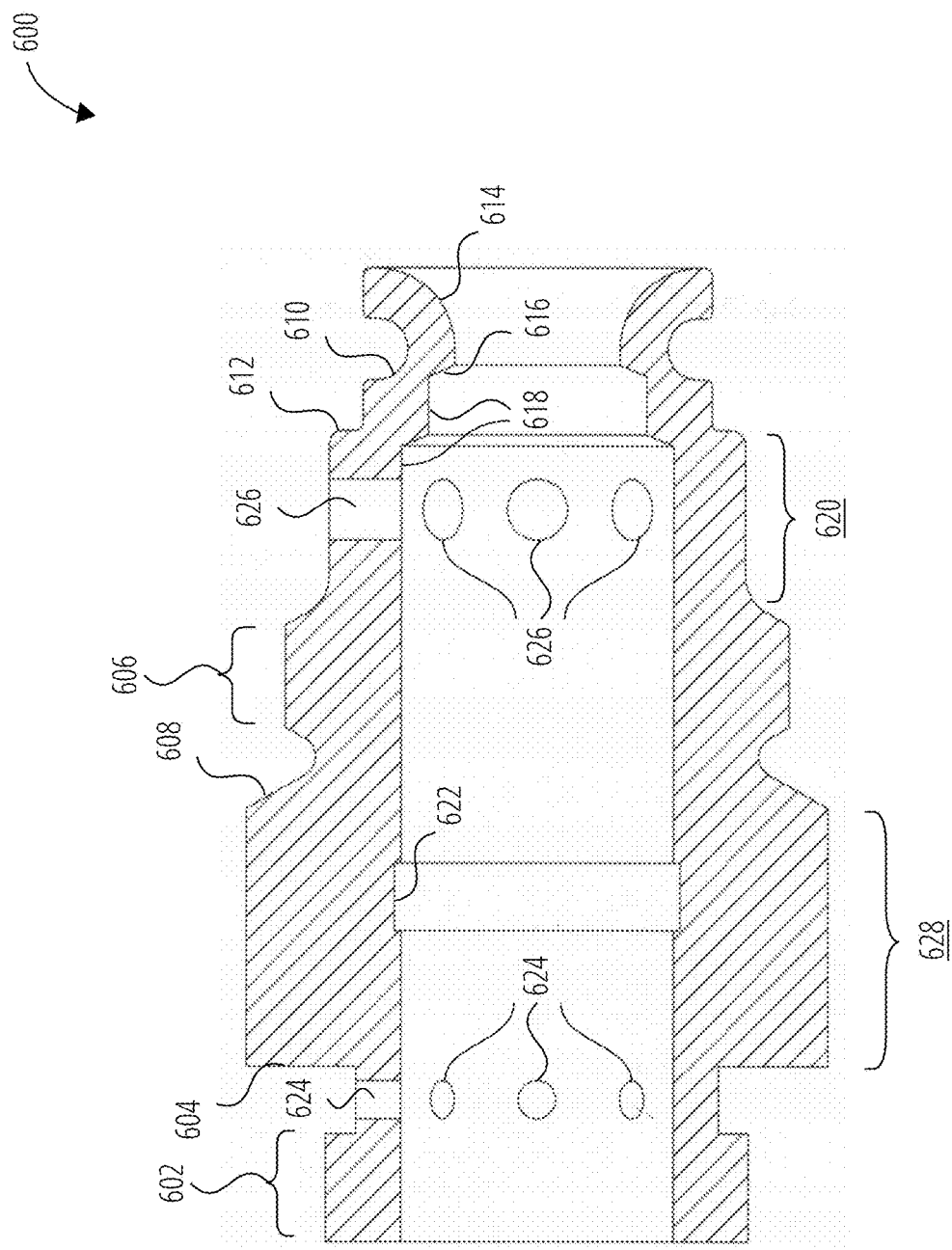
FIG. 6 illustrates a side section view of a vaporizer body 600 in accordance with one embodiment.

Referring to FIG. 6, a side section view of a vaporizer body 600 is illustrated in an embodiment. The battery attachment threads 602 indicate threads where the battery attaches. A battery abutment surface 604 indicates the surface against which the battery butts up. The mouthpiece threads 606 indicate threads onto which the mouthpiece screws. A mouthpiece abutment 608 indicates a tapered surface that mates up to a corresponding tapered surface on the edge of the mouthpiece. This may create an airtight seal so that suction from the air hole in the mouthpiece may be drawn through the vaporizer assembly. An o-ring groove 610 indicates a groove for the first o-ring 502.

A cartridge abutment 612 indicates a surface to which the cartridge abuts when it is attached to the vaporizer assembly. A flow medium director 614 indicates a curved surface that directs the flow of the liquid medium from inside the reservoir to the ceramic heating element. This curved surface may allow for this area to be easily cleaned. It may also assist in relieving surface tension in the liquid medium so that as little as possible is wasted and may allow for a more thorough emptying of the liquid medium before the cartridge is replaced, or refilled. An inner o-ring sealing surface 616 indicates a surface against which the inner O-ring seals. A heating element centering surface 618 indicates surfaces that help center the ceramic heating element within the vaporizer body. A mouthpiece guide 620 indicates an area that helps guide the mouthpiece onto the vaporizer body when attaching the mouthpiece and also provides for a void between the mouthpiece and the vaporizer body to allow vapor to travel down toward the air hole end of the mouthpiece. An internal groove 622 indicates an internal groove around the inside of the vaporizer body for the lock ring to engage holding the assembly together, e.g., lock ring 310. The fresh air intake holes 624 indicate air intake holes on the vaporizer body. A plurality of exhaust holes 626 indicate exhaust holes in the vaporizer body from which air and vapor escape to be drawn through the mouthpiece around the cartridge and out of the mouthpiece hole. A flat surface 628 indicates a flat surface on the outside of the vaporizer body, explained in greater detail in FIG. 13 below.

Figure 7:
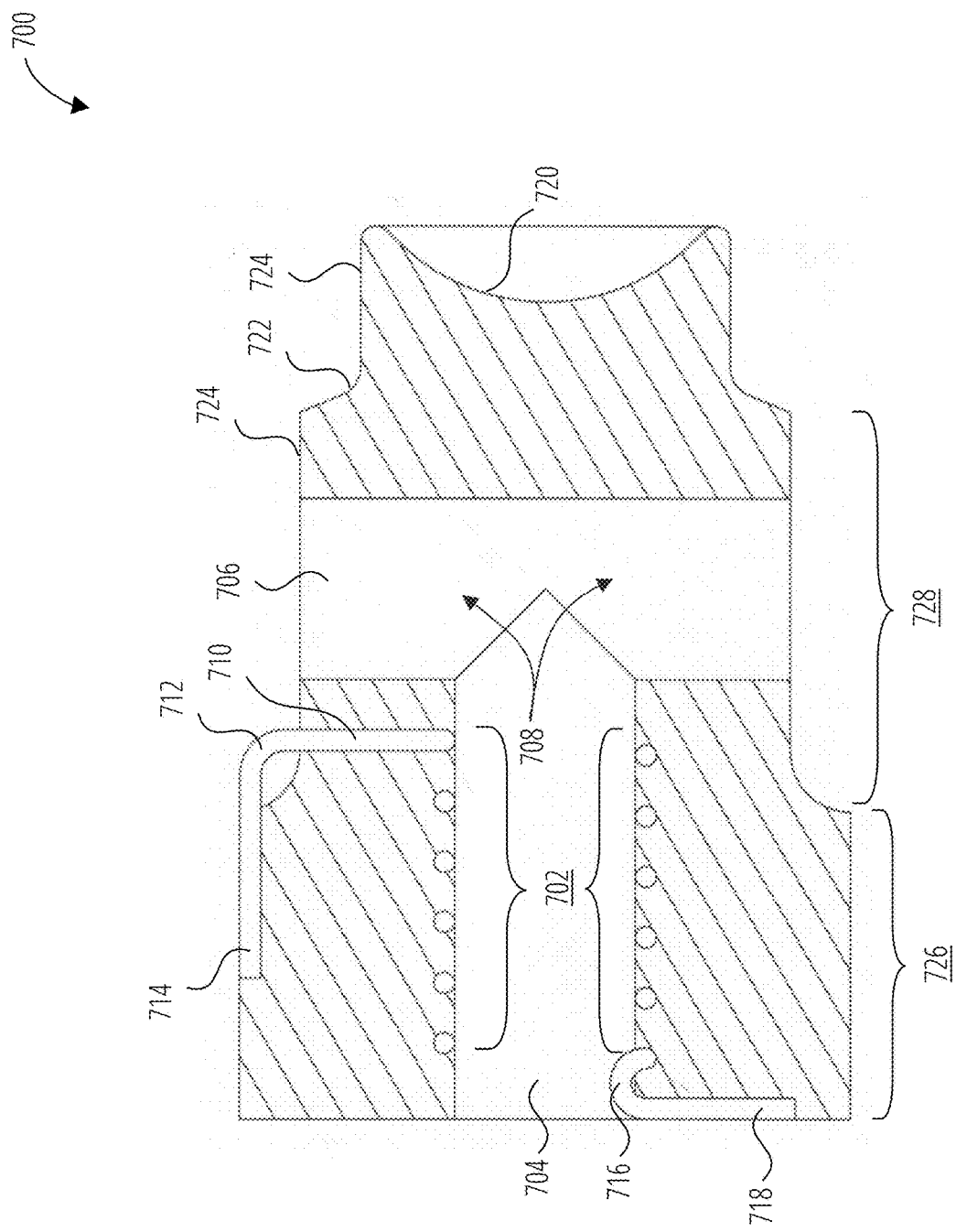
FIG. 7 illustrates a section view of the heating element 700 in accordance with one embodiment.

Referring to FIG. 7, a section view of the heating element 700 shows the inner workings of one embodiment of heating element, which may be made of a porous ceramic material. It may allow the liquid medium to be absorbed at the cartridge reservoir and to be transferred through the ceramic to the heating element where it is vaporized. A heating coil 702 may be a heat resistant metal coil embedded into the material surrounding the air passageway. Fresh air flow 704 represents a location where fresh air enters the heating element. An air exit 706 shows where air and vapor exit the heating element. Air leaving heating element 708 shows where air and vapor leave the heating element and flow through the cross hole to leave the heating element. A negative heating coil lead 710 represents the negative lead of the heating coil, embedded in the material and coming out of the side of the heating element. A negative lead connection to vaporizer body 712 indicates a point at which the negative lead is bent over and laid next to the large diameter of the centering contact 726 of the heating element. A negative lead connection 714 indicates where the negative lead is bent over and laid parallel to the centerline of the part on the outside of the part where it will contact the inner bore of the vaporizer body and complete the circuit.

A positive heating coil lead bend 716 and positive heating coil lead 718 show where the positive lead of the heating coil bends over and rests against the bottom of the heating element. The positive heating coil lead 718 may be cut short enough to where it will not be able to contact the inner border of the vaporizer body creating a short circuit. The center conductor comes in contact with this positive lead to complete the circuit. A surface 720 represents the surface of the heating element material that comes in contact with the liquid inside the cartridge reservoir. The liquid may soak into the surface. This surface may be curved as shown, or flat. It is shown curved to create more surface area for better absorption of the liquid medium. The second seal 722 indicates an area that seals against the second o-ring. A centering element 724 indicates an area that contacts the inner bore of the vaporizer body and centers the two parts along the same centerline. A recessed area 728 indicates an area that is recessed and creates a void between the ceramic heating element and vaporizer body creating an exhaust air cavity for the air and vapor to circulate and escape through the plurality of exhaust holes in the vaporizer body.

Figure 8:
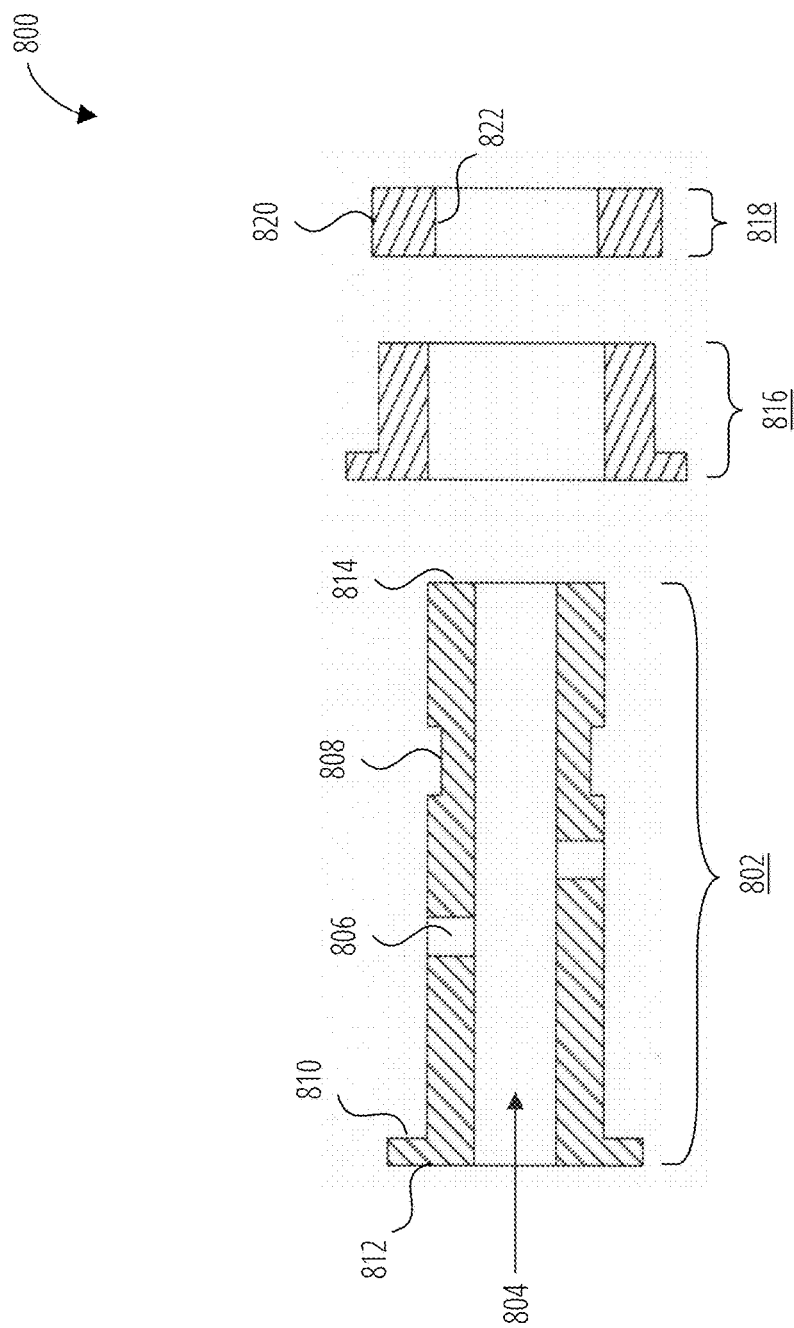
FIG. 8 illustrates a section view of a center conductor, insulator bushing, and lock ring 800 in accordance with one embodiment.

FIG. 8, a section view of a center conductor, insulator bushing, and lock ring 800 shows the center conductor 802, the insulator bushing 816 and the lock ring 818. An air passage 804 indicates the main air passage through the center of the center conductor. This passage is also where air may enter from the battery to actuate a suction switch on the battery assembly. A plurality of air holes 806 indicates air holes through the sides of the center conductor 802 that allow air to pass from the outside to the inside of the center conductor 802. A groove in the center conductor 808 indicates where the lock ring 818 engages. The surface has a smaller diameter than the inner diameter of the lock ring 818. A third center conductor surface 810 indicates a surface that contacts the insulator bushing 816 and may prevent the insulator bushing 816 from sliding off the end of the center conductor 802 when the vaporizer assembly is assembled. A first center conductor surface 812 indicates a surface that contacts the positive contact on the battery. A second center conductor surface 814 indicates a surface that contacts the ceramic heating element. The surface may also complete the circuit between the center conductor 802 and the positive lead on the ceramic heating element.

Referring to the insulator bushing 816 and lock ring 818, a lock ring outer surface 820 is the outer surface of the lock ring 818 that engages the groove in the vaporizer body. A lock ring inner surface 822 represents the inner surface of the lock ring that engages with the groove in the center conductor. One non-limiting method for assembling the vaporizer assembly is as follows. A first o-ring is placed over the O-ring groove on the outside of the vaporizer body. A second o-ring is slipped over the end of the ceramic heating element. The negative heating coil lead folds down the side of the heating element and the heating element slides into the bore in the vaporizer body. The insulator bushing 816 slides over the outside of the center conductor 802 until it contacts the third center conductor surface 810. The lock ring 818 slides over the outside of the center conductor 802 and slides until it drops into the groove in the center conductor 808, an interference fit. Clearance exists between the inner diameter of the lock ring 818 and the outer diameter of the groove in the center conductor 808, allowing the lock ring 818 to be compressed when it is attached to the center conductor 802. This allows the lock ring 818 to be compressed and pressed into the end of the bore of the vaporizer body. When the center conductor 802, insulator bushing 816, and lock ring 818 assembly presses into the end of the vaporizer body and reaches the point where the lock ring 818 and the groove on the inside of the vaporizer body align, the lock ring 818 expands into the groove in the vaporizer body, thereby locking the entire vaporizer assembly in place. When this occurs, compression on the second o-ring between the ceramic heating element and the vaporizer body may create a liquid tight seal.

Figure 9:
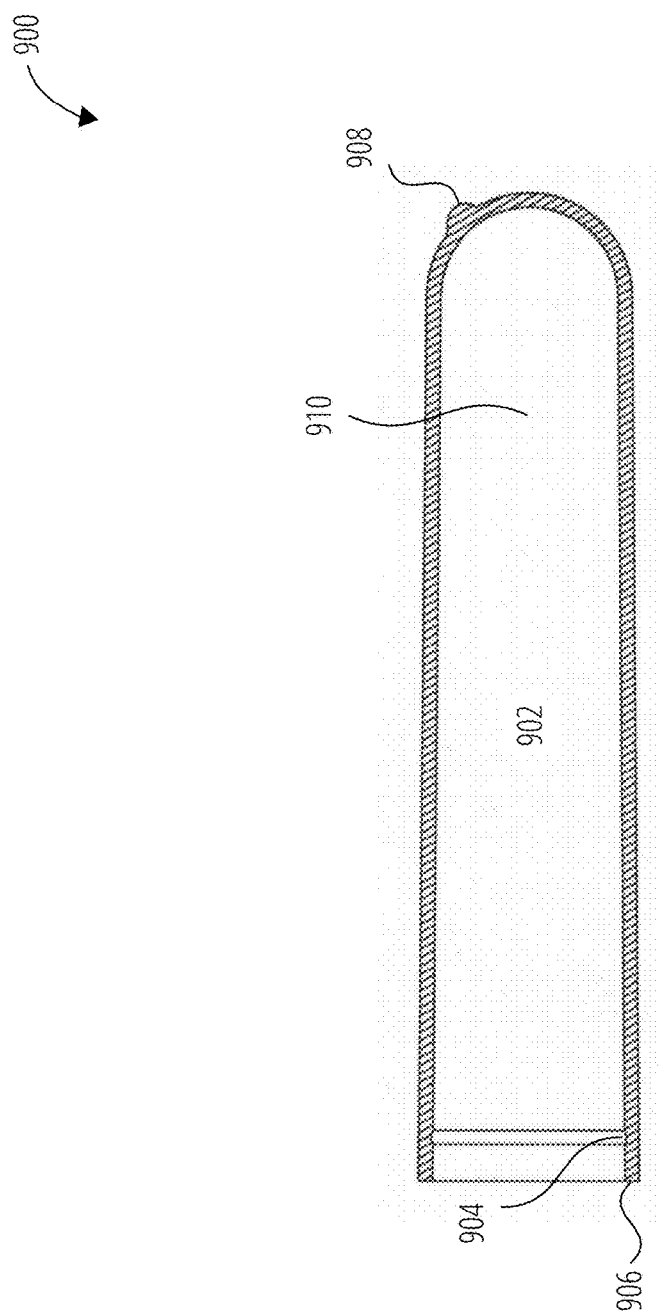
FIG. 9 illustrates a side view of a cartridge of the vaporizer cartridge system 900 in accordance with one embodiment.

FIG. 9, a side view of a cartridge of the vaporizer cartridge system 900, shows an exemplary cartridge for holding the liquid medium according to one embodiment. The cartridge may be constructed from one or more materials, for example food grade materials such as HDPE or another material. The cartridge may be selectively attached onto the vaporizer assembly such that it is in fluid communication, and covered with the mouthpiece. A clearance between the outside of the cartridge in the inside of the mouthpiece allows air and vapor to travel around the cartridge from the vaporizer assembly to the air hole in the mouthpiece. Liquid 902 indicates a cavity inside a reservoir 910 where the liquid medium is stored. Liquid may exit the cavity via an outlet of the cartridge. The groove 904 represents an O-ring groove that helps hold the cartridge on to the vaporizer assembly. It also creates a liquid tight first seal between the cartridge and the vaporizer body. An outer surface 906 represents a surface contacting the cartridge abutment 612 surface in FIG. 6, keeping the cartridge positioned against the vaporizer body and trapping the cartridge between the cartridge abutment 612 in FIG. 6 and a mouthpiece surface 1012.

A bump 908 represents a protrusion on the end of the cartridge. It may be any shape, e.g., for utility or ornamental purposes. The number of raised bumps may vary between embodiments from about one bump to about twenty bumps, for example 2 bumps, 3 bumps, 4 bumps, 5 bumps, 6 bumps, 10 bumps, 15 bumps, or any other number of bumps in that range. Each bump may also contact the surface shown by the mouthpiece surface 1012. This may create a void between the mouthpiece surface 1012 and the outer surface of the cartridge. This configuration may also allow air and vapor to circulate around the outside of the cartridge inside the mouthpiece and may prevent the cartridge from blocking the vapor intake 1006 in the mouthpiece.

In some embodiments, the cartridge may not include additional structures aside from a cap and O-ring in order to minimize cost. In some embodiments, the cartridge may include one or more visual visible markers (e.g., a visible bump, line, or other visible structure) on an exterior or interior surface, the visual visible markers corresponding with liquid fill volumes.

In some embodiments, the cartridge may be supplied with a closure to hold in the liquid. In an embodiment, this closure may be a foil or plastic closure. In an embodiment, the closure is punctured or cut prior to installing the cartridge in the vaporizer cartridge system. In another embodiment, the closure on the cartridge is not punctured or torn by a device on the vaporizer cartridge system.

Figure 10:
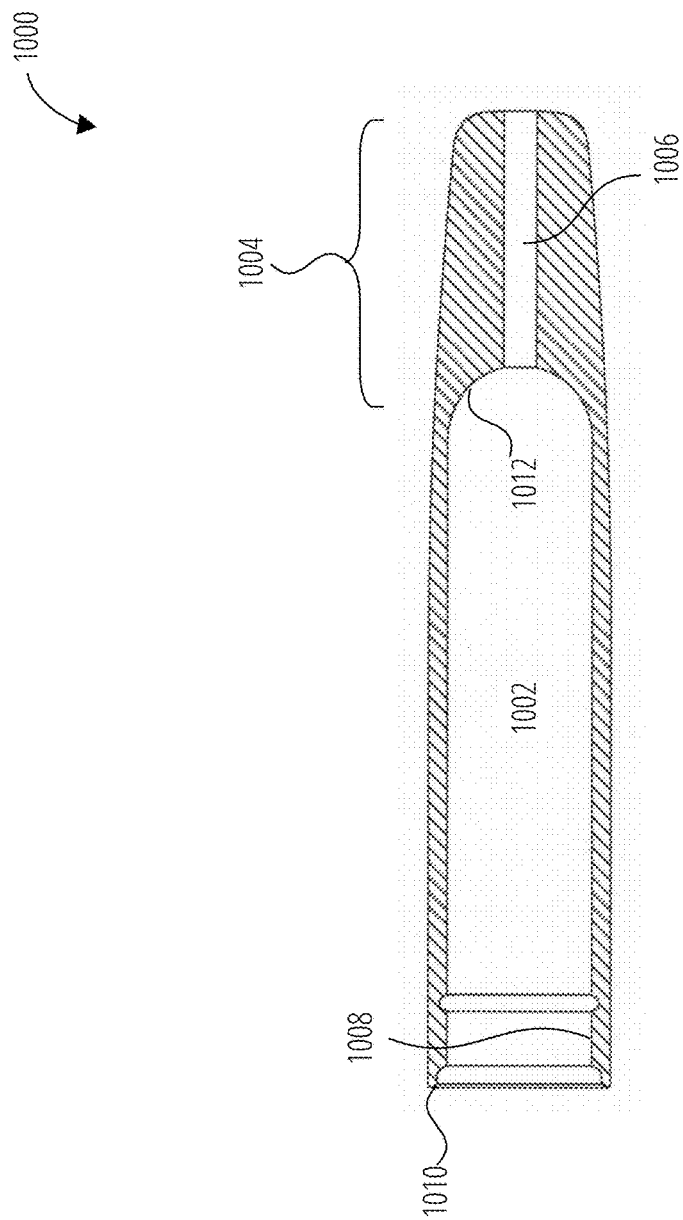
FIG. 10 illustrates a side view of a mouthpiece of the vaporizer cartridge system 1000 in accordance with one embodiment.

FIG. 10, a side view of a mouthpiece of the vaporizer cartridge system 1000 according to an embodiment, illustrates the mouthpiece that fits over the cartridge, located within the mouthpiece cavity 1002, and secures to the vaporizer. The mouthpiece comprises a mouthpiece end 1004 through which vapor passes through a vapor intake 1006. A mouthpiece surface 1012 comprises a surface within the mouthpiece where the cartridge typically includes a protruding bump 908 (see above) allowing air flow between the cartridge and mouthpiece.

A set of vaporizer threads 1008 match the corresponding mouthpiece threads 606 on the vaporizer assembly described in FIG. 6 above allowing the mouthpiece to screw onto the vaporizer body. A vaporizer body abutment 1010 forms a connection with the mouthpiece abutment 608 described above and illustrated under FIG. 6 where the mouthpiece and vaporizer body meet when the mouthpiece as shown screws onto the vaporizer assembly.

Figure 11:
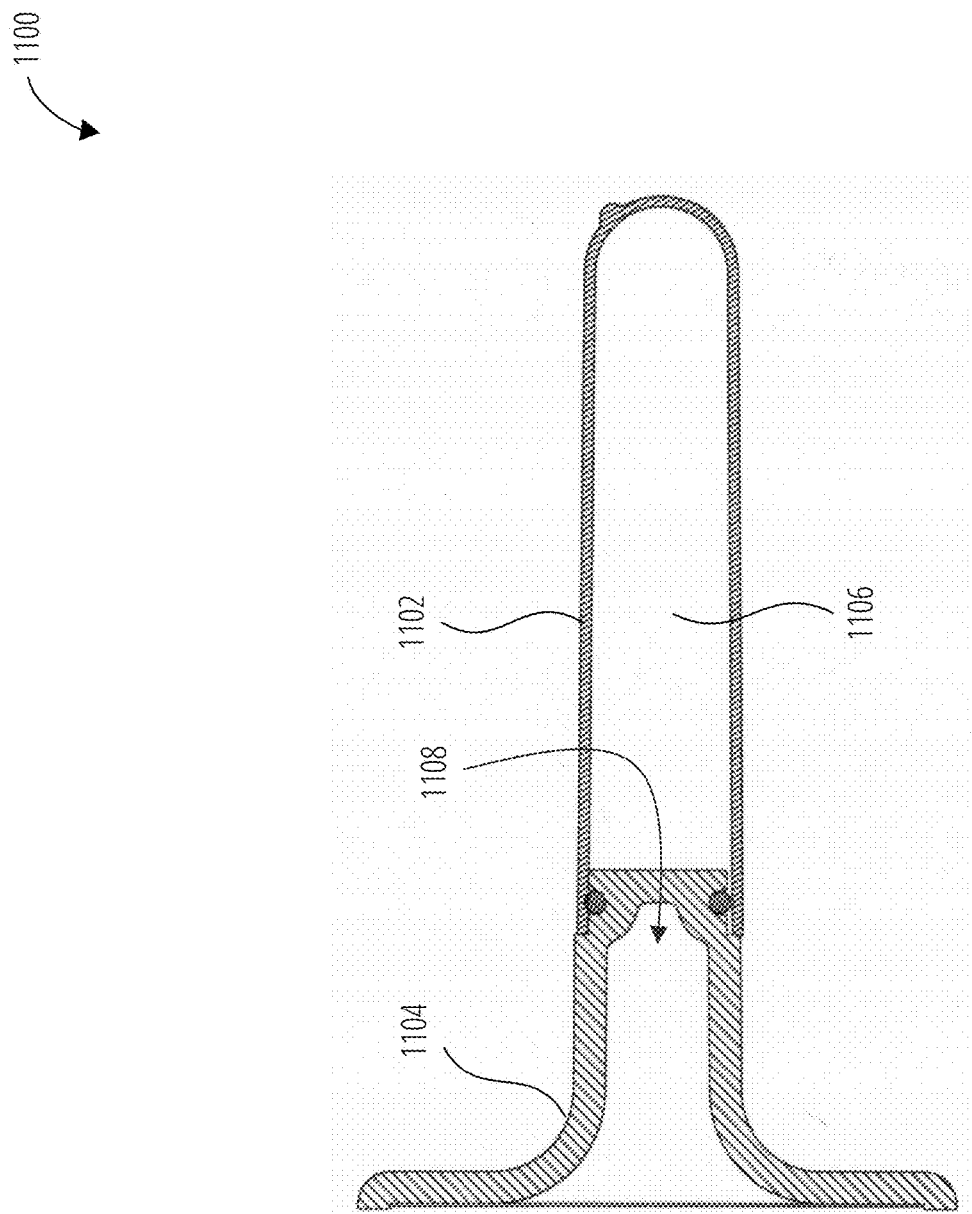
FIG. 11 illustrates a side view of a vaporizer cartridge assembly 1100 in accordance with one embodiment.

FIG. 11, a vaporizer cartridge assembly 1100 according to an embodiment, shows the cartridge 1102 and a cap 1104 for plugging the cartridge reservoir 1106. The cap 1104 may be configured to physically plug an outlet 1108 of liquid from the cartridge 1102. The cap 1104 may also facilitate storage and shipment of the cartridge refill. The cap 1104 may have any shape and may also have a flat surface that allows the vaporizer cartridge assembly 1100 to rest on (e.g., stand upright) on a flat surface. Any part of the cap 1104 may form at least part of a grasping portion to enable removal of the cap from the cartridge.

Figure 12:
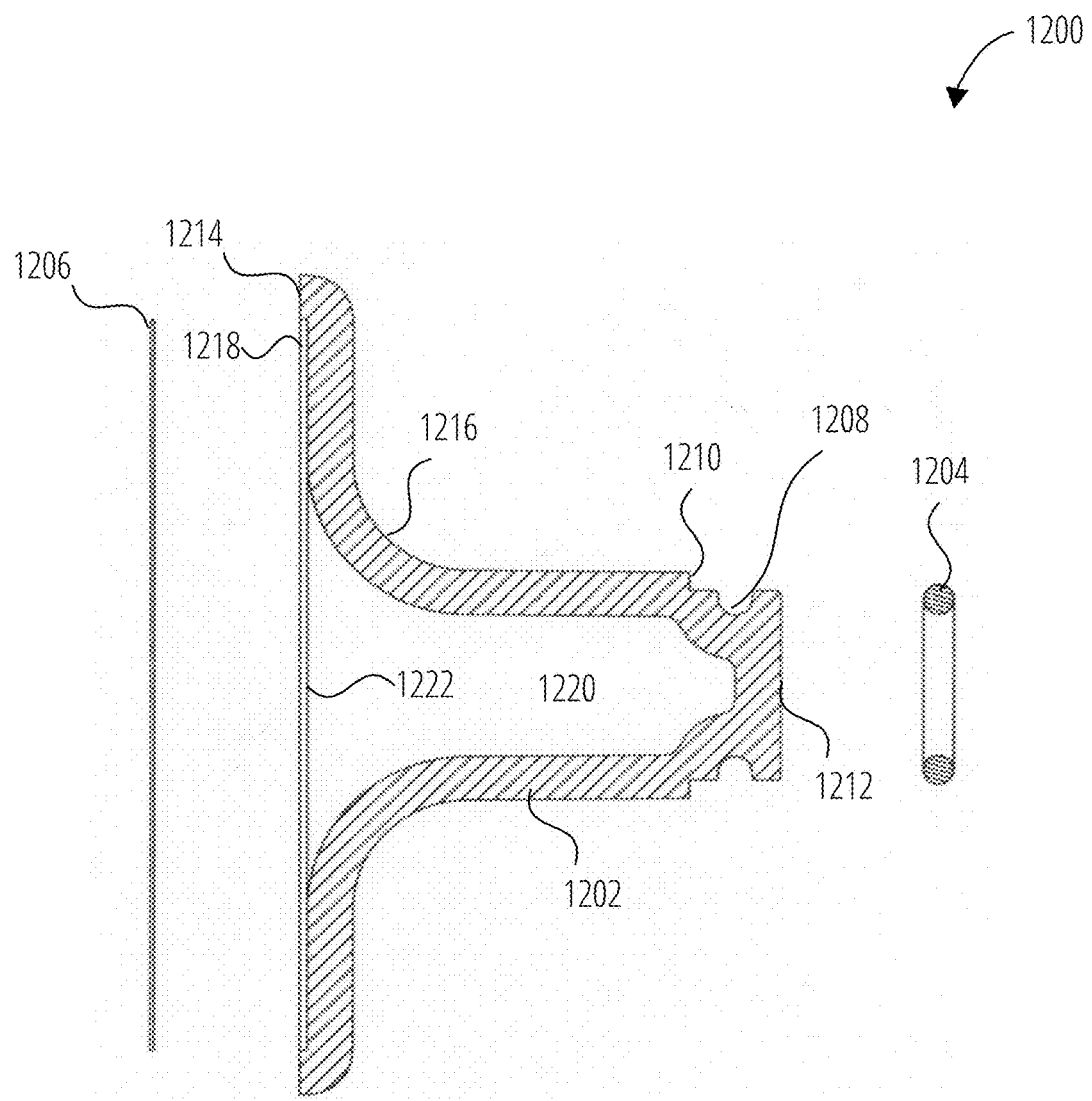
FIG. 12 illustrates an exploded side section view of a cartridge cap 1200 in accordance with one embodiment.

FIG. 12, an exploded side section view of a cartridge cap 1200, shows an exploded view of the cap. A cap body 1202 indicates the extent of the cap. The first o-ring 1204 is an O-ring to seal the cap body to the cartridge. In some embodiments, the first o-ring 1204 may be substituted for a raised rib that may be molded into the cap body in place of the groove 1208 to seal the cap body to the cartridge.

An emblem 1206 is an optional decal or appliqué. This emblem 1206 may show the contents of the cartridge reservoir to which the plug attaches. The emblem 1206 may also show company logos, the variety of liquid medium, etc.

A groove 1208 is an O-ring groove. A surface 1210 indicates a surface for the outer surface 906 to contact and position the cartridge reservoir and the assembly together. A liquid contact surface 1212 indicates a flat surface that will be exposed to the liquid inside the cartridge reservoir, flat for ease of cleaning when the cap is removed from the cartridge reservoir. A surface 1214 is a flat surface on the body, allowing the cartridge to be placed on a flat surface with the cartridge reservoir facing upward and preventing the cartridge refill assembly from rolling around on a table or other flat surface. The edge of the flat surface may have any shape, for example any design such as a logo outline or any type of polygon, etc.

A handle surface 1216 indicates a radius or fillet that is to provide a good feel in the hands while pulling the cap off of the cartridge reservoir. A flat surface 1218 indicates where an emblem 1206 may be applied. A cap interior 1220 shows a space within the cap body 1202 allowing for a consistent wall thickness for injection molding. An emblem center 1222 shows the unsupported center part of the emblem 1206. The emblem 1206 covers this and makes the flat surface 1218 appear flat.

The cap may be of any non-reactive material, e.g., lightweight metal or molded plastic, able to be molded or die-cast into a shape suitable for plugging the outlet end of the cartridge holding liquid, as with the groove 1208.

Figure 13:
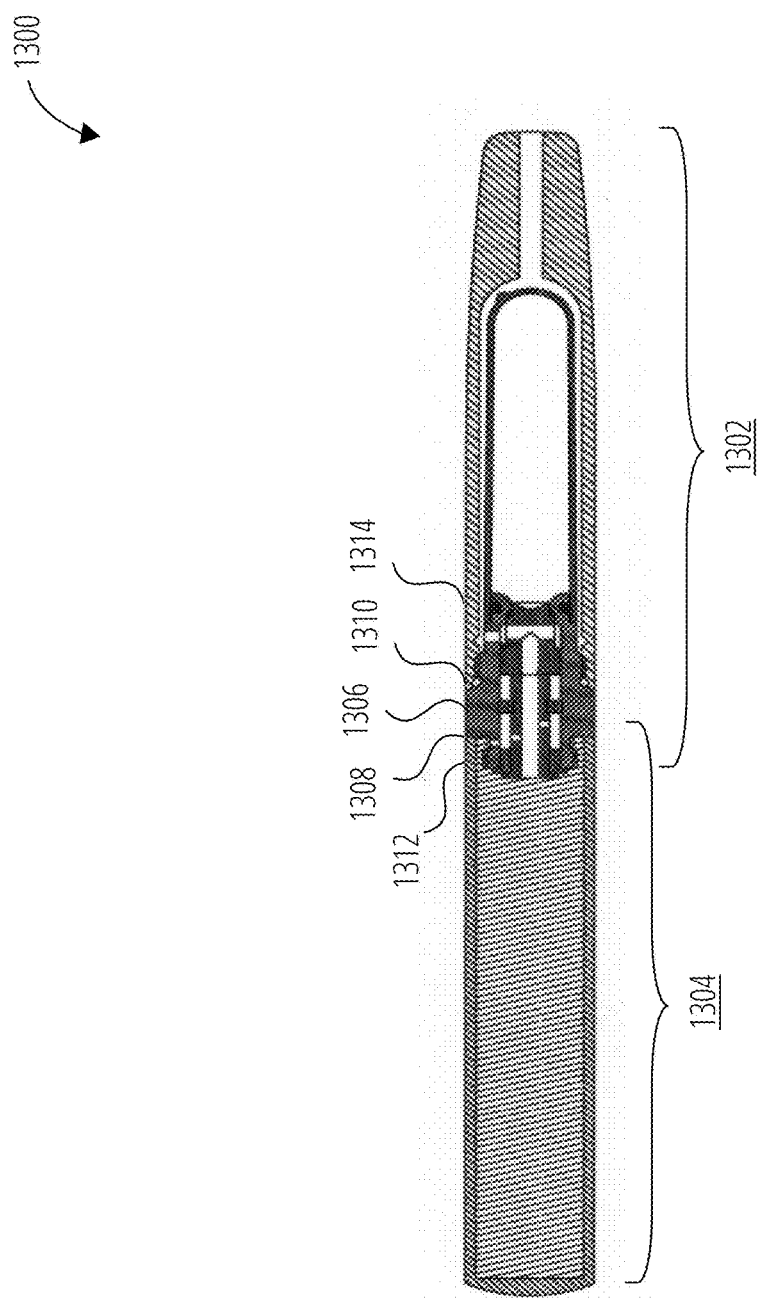
FIG. 13 illustrates a side section view of a representative vaporizer cartridge system 1300 in accordance with one embodiment.

FIG. 13, a side section view of a representative vaporizer cartridge system 1300 according to one embodiment, shows the complete vaporizer device with the battery attached. The vaporizer assembly 1302 indicates the vaporizer assembly with the cartridge and mouthpiece attached. A battery assembly 1304 includes the battery. A flat surface 1306 mirrors the flat surface 628 discussed above under FIG. 6. This surface may represent an ornamental design element as well as functional and may provide one or more of the following benefits: mimicking the band often found on cigars; setting with stones, having a decal applied, or being engraved; providing a place to hold while unscrewing the battery; and, providing a place to hold while unscrewing the mouthpiece. A battery interface 1308 shows the interface and seam between the vaporizer assembly and the battery assembly 1304. A mouthpiece interface 1310 shows the interface and seam between the vaporizer assembly and the mouthpiece. A battery holding area 1312 shows where one may hold the battery, e.g., in one hand, while holding the flat surface 1306 in the other hand to unscrew the battery. A mouthpiece holding area 1314 shows where one may hold the mouthpiece in one hand and the vaporizer body in the other hand at the flat surface 1306 to unscrew the mouthpiece.

Figure 14:
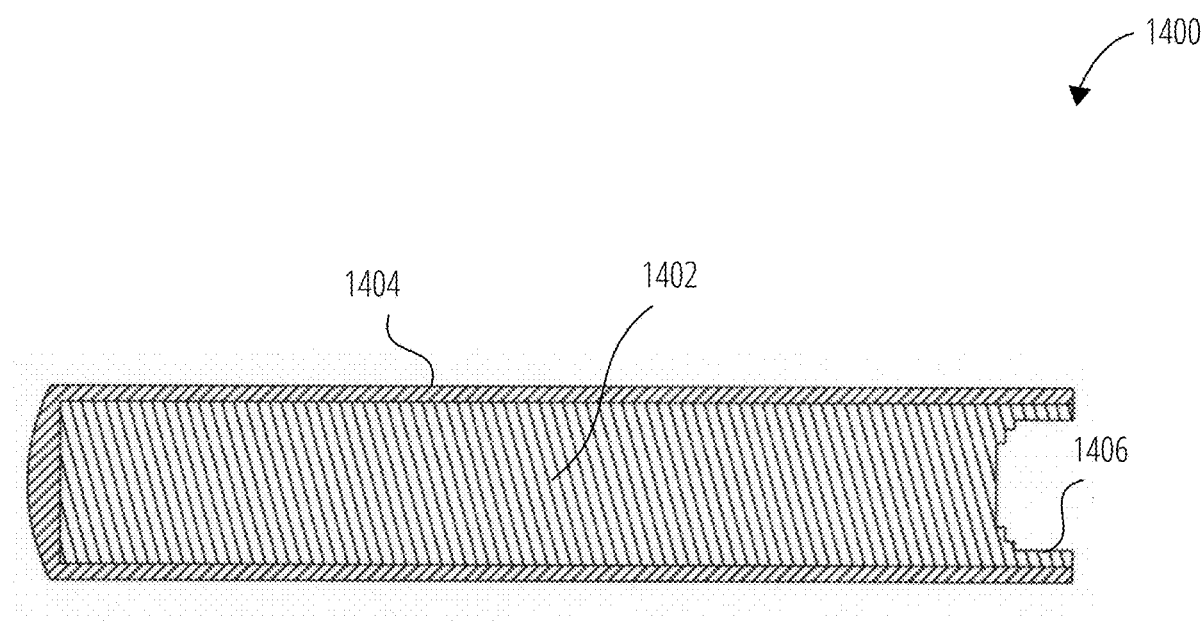
FIG. 14 illustrates a side section view of a battery assembly 1400 in accordance with one embodiment.

FIG. 14 shows a side section view of a battery assembly 1400 according to one embodiment. The battery assembly may include a battery, a suction switch mechanism, a charging connector, and any electronics needed for battery related process and recharging the battery. A battery 1402 with a modular battery cover 1404 is shown. The battery cover allows a user to match it to the mouthpiece and change out the mouthpiece and the battery cover without having to replace the entire unit, e.g., to change the look of the vaporizer cartridge system, or for easier serviceability. The battery cover 1404 may be made out of one or more of a variety of materials, including precious metals. The battery threads 1406 show the threads attaching the battery assembly to the vaporizer assembly. Reasons for having a battery cover and separate battery unit may include, but are not limited to: a user wanting to keep the battery cover 1404 and yet desiring an updated battery 1402 because the current battery unit may be obsolete. A user may also change the battery cover 1404 without changing the battery 1402.

The battery assembly comprises a battery powering the vaporizer assembly. In an embodiment, the battery may supply about 3.0 V-12.0 V, but is not limited thereto. The battery may have leads (positive and negative) adapted to be exposed to the center conductor and the vaporizer body. The battery 1402 or battery cover 1404 may be made of any moldable material able to accommodate cut-in threads for attaching the battery assembly to the vaporizer assembly.

The battery cover may be of any durable material, e.g., rubber, non-reactive metal, plastic, ceramic, etc., suitable for sliding over the battery assembly. As noted above, the cover material may be particularly durable as a user may choose to retain the battery cover when acquiring or replacing a new battery unit.

The battery may be a rechargeable battery that is chargeable using the charging connector. Typically, the charging connector is a USB type connector. In an embodiment, the rechargeable battery may be charged without removing the battery assembly from the vaporizer cartridge system. In another embodiment, the battery assembly is removed from the vaporizer cartridge system for recharging. In yet an additional embodiment, the battery is removed from the battery assembly for recharging in an external charging device.

In some embodiments, the battery and/or battery assembly, may include functionality to communicate with a smartphone, tablet, or computer through Bluetooth or some other wireless, or wired protocol to allow control through an app on the smartphone, tablet, or computer. Examples of functionality that may be accessed through an app include, but are not limited to, parental controls, adjusting heat settings for the heating element, presets for different types and brands of vaporizing liquid, checking battery life, device usage data, and device diagnostics.

In some embodiment, the battery and/or battery assembly may also allow the user to adjust some functionality and settings without connecting to an external device. This may be accessed through a button or buttons on the battery and/or battery assembly and may also include an LED indicator or a display for user feedback from the battery. The ability to control functions on the battery without the use of a smartphone, tablet, or computer may be useful to users who prefer to use the device without sharing personal information or using advanced features.

Figure 15:
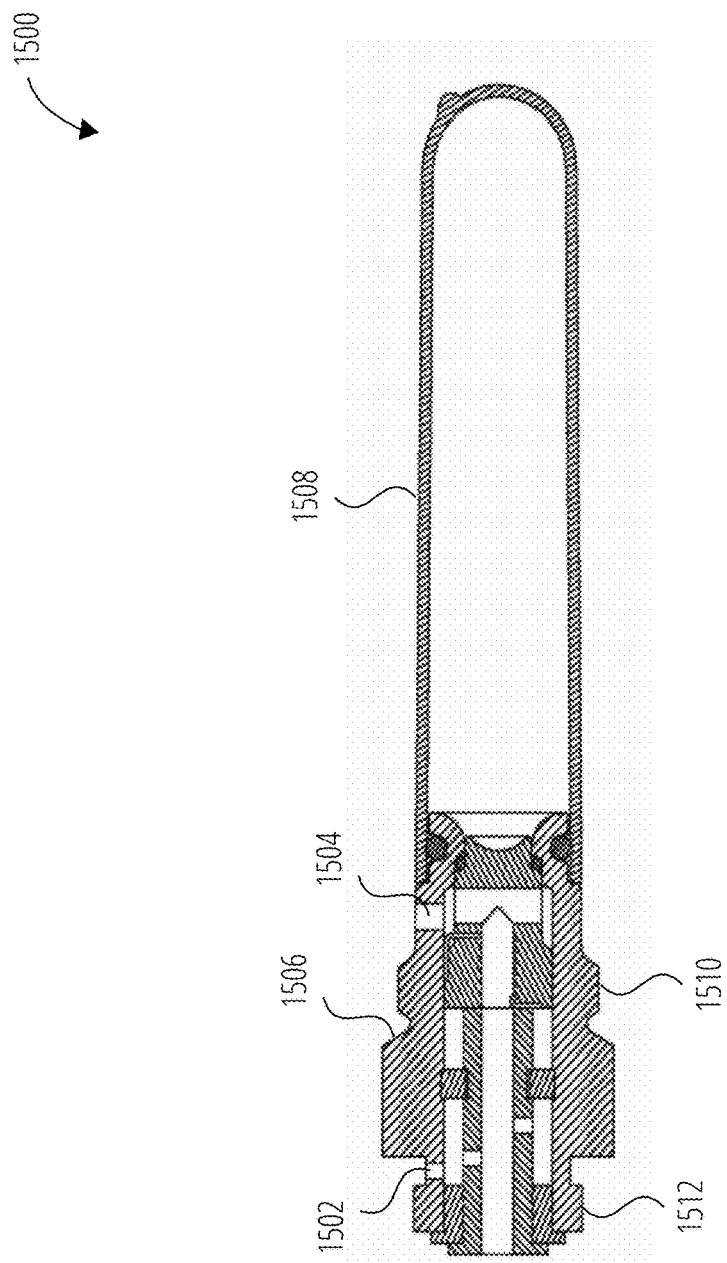
FIG. 15 illustrates a partial side section view of a vaporizer cartridge system 1500 in accordance with one embodiment.

Referring to FIG. 15, a partial side section view of a vaporizer cartridge system 1500 according to an embodiment is shown, illustrating how the components described above fit together. With the vaporizer assembly and cartridge 1508 now fitted together, the first taper 1506 and second taper (shown on FIG. 10 as vaporizer body abutment 1010) form a seal with the mouthpiece, allowing air to be drawn through a first hole 1502, past the heating coil and picking up vapor and passing out of a second hole 1504. The first taper 1506 and second taper create the seal allowing air to be drawn around the cartridge 1508 and out the end of the mouthpiece. The vaporizer assembly additionally comprises battery assembly threads 1512 and external threads 1510, allowing the battery assembly and mouthpiece to screw onto the vaporizer assembly.

Figure 16:
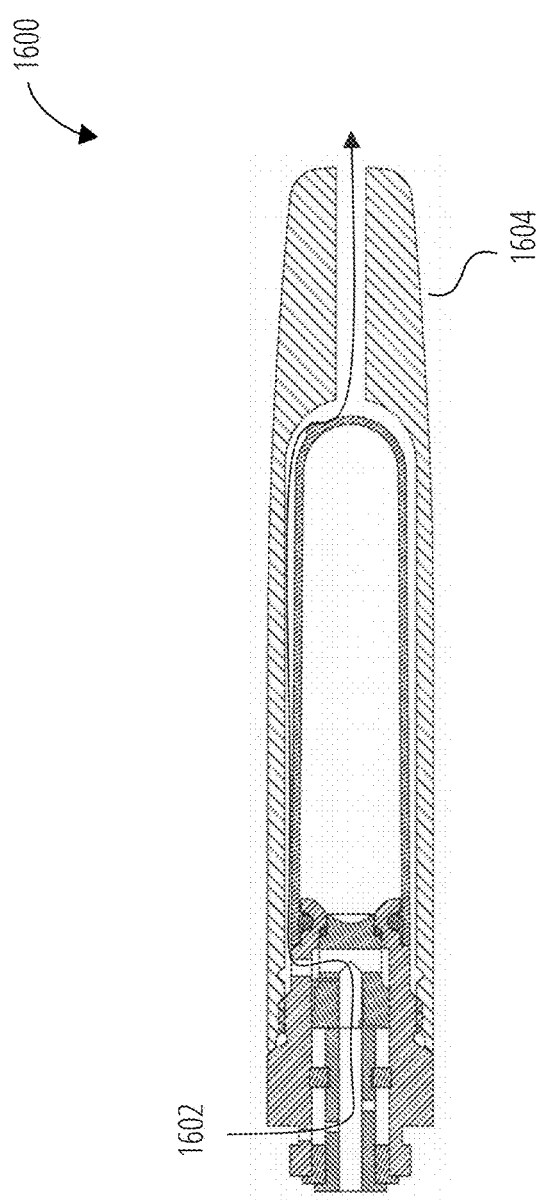
FIG. 16 illustrates a partial side section view of a vaporizer cartridge system 1600 in accordance with one embodiment.

Referring to FIG. 16, a partial side section view of a vaporizer cartridge system 1600 according to an embodiment, illustrates an air flow 1602 through the vaporizer assembly, around the cartridge, and out the mouthpiece 1604.

While illustrative embodiments have been illustrated and described, it will be appreciated that various changes can be made therein without departing from the spirit and scope of the invention. In particular, aspects from various embodiments may be incorporated into other embodiments.

What is claimed is:
1. A vaporizer cartridge system, comprising:
a vaporizer assembly comprising:
a vaporizer body comprising a plurality of fresh air intake holes;
a heating element selectively attachable with the vaporizer body,
the heating element comprising:
a heating element body comprising a porous ceramic material;

a heating element cavity in fluid communication with the plurality of fresh air intake holes in the vaporizer body;

a heating coil surrounding the heating element cavity;

a liquid contact surface in contact with a liquid inside a reservoir;

a heating element exhaust passage through the heating element body and in fluid communication with the heating element cavity and a plurality of exhaust holes in the vaporizer body, wherein the heating element exhaust passage is substantially perpendicular to the heating element cavity;

an insulator bushing selectively attachable with the vaporizer body;

a center conductor selectively attachable with the insulator bushing and a lock ring;

the lock ring located between grooves in the vaporizer body and grooves in the center conductor;

a first seal between the vaporizer body and a cartridge; and a second seal between the vaporizer body and the heating element;

a mouthpiece that is selectively attachable with the vaporizer assembly;

a battery assembly including a battery, the battery assembly selectively attachable with the vaporizer assembly; and a cartridge including a reservoir, the cartridge configured to store a liquid in the reservoir, the cartridge being selectively attachable with the vaporizer assembly such that the liquid stored within the reservoir is in fluid communication with the vaporizer assembly, wherein the vaporizer cartridge system is configured such that when the cartridge and the mouthpiece are attached to the vaporizer assembly, the cartridge fits within the mouthpiece.

2. The vaporizer cartridge system of claim 1, wherein the lock ring is configured to expand into the grooves in the vaporizer body.

3. The vaporizer cartridge system of claim 2, wherein the lock ring is constructed of silicone.

4. A vaporizer cartridge system, comprising: a vaporizer assembly comprising:

a vaporizer body comprising a plurality of fresh air intake holes;

a heating element selectively attachable with the vaporizer body, the heating element comprising:

a heating element body comprising a porous ceramic material;

a heating element cavity in fluid communication with the plurality of fresh air intake holes in the vaporizer body and a center conductor cavity;

a heating coil surrounding the heating element cavity;

a liquid contact surface in contact with a liquid inside a reservoir;

a heating element exhaust passage through the heating element body and in fluid communication with the heating element cavity and a plurality of exhaust holes in the vaporizer body, wherein the heating element exhaust passage is substantially perpendicular to the heating element cavity;

an insulator bushing selectively attachable with the vaporizer body;

a center conductor selectively attachable with the insulator bushing and a lock ring, the center conductor comprising:

the center conductor cavity; and a plurality of air holes through a wall of the center conductor, wherein the plurality of air holes are in fluid communication with the center conductor cavity and a space between the plurality of air holes, the center conductor, the insulator bushing, and the lock ring, wherein the space between the plurality of air holes is in fluid communication with the plurality of fresh air intake holes in the vaporizer body;

the lock ring located between grooves in the vaporizer body and grooves in the center conductor;

the lock ring configured to expand into the grooves in the vaporizer body;

a first seal between the vaporizer body and a cartridge; and a second seal between the vaporizer body and the heating element, adjacent to the liquid contact surface of the heating element and opposite a battery assembly on the heating element, wherein the second seal is a liquid tight seal;

a mouthpiece that is selectively attachable with the vaporizer assembly;

the battery assembly including a battery, the battery assembly selectively attachable with the vaporizer assembly; and a cartridge including the reservoir, the cartridge configured to store the liquid in the reservoir, the cartridge being selectively attachable with the vaporizer assembly such that the liquid stored within the reservoir is in fluid communication with the vaporizer assembly, wherein the vaporizer cartridge system is configured such that when the cartridge and the mouthpiece are attached to the vaporizer assembly, the cartridge fits within the mouthpiece, wherein the heating element is configured to:

vaporize, inside of the heating element cavity, at least a portion of the liquid inside of the heating element cavity;

combine, inside of the heating element cavity, the vaporized portion of the liquid with fresh air from the plurality of fresh air intake holes; and exhaust the combined vaporized portion of the liquid and fresh air through the heating element exhaust passage.

5. The vaporizer cartridge system of claim 4, wherein the vaporizer body further comprises:

an exhaust air cavity inside of the vaporizer body, dimensioned to accept the heating element, the insulator bushing, the center conductor, and the lock ring; and the plurality of exhaust holes in the vaporizer body, wherein the plurality of exhaust holes are in fluid communication with the exhaust air cavity and the mouthpiece.

6. The vaporizer cartridge system of claim 4, wherein the center conductor further comprises:

a groove in the center conductor for engaging the lock ring;

a first center conductor surface that contacts a positive contact on the battery assembly;

a second center conductor surface that contacts the heating element; and a third center conductor surface that contacts the insulator bushing.

7. The vaporizer cartridge system of claim 4, wherein the heating coil comprises:

a positive heating coil lead in contact with the center conductor, and a negative heating coil lead in contact with the vaporizer body.

8. The vaporizer cartridge system of claim 4, wherein the porous ceramic material allows the liquid to permeate into the heating element body allowing vaporization of at least a portion of the liquid by the heating coil.

9. The vaporizer cartridge system of claim 4, wherein the first seal and the second seal each comprise an o-ring.

10. The vaporizer cartridge system of claim 4,
wherein the battery assembly is configured to allow fresh air to enter through the battery assembly;
the battery assembly is in fluid communication with the center conductor cavity, and
the battery assembly includes a rechargeable battery, a suction switch mechanism, and a charging connector, wherein the suction switch mechanism is configured to actuate the battery upon entry of air through the battery assembly.

11. The vaporizer cartridge system of claim 4, further comprising a cap configured to removably plug an outlet for the liquid of the cartridge.

12. The vaporizer cartridge system of claim 4, with the proviso that the vaporizer cartridge system does not include a cutting device or a puncturing device for at least partially opening or removing a closure on the cartridge.

13. The vaporizer cartridge system of claim 4, wherein the cartridge includes one or more visible markers on an exterior or interior surface, wherein the visual markers correspond to liquid fill volumes, and the visible markers include at least one of a bump and a line.

14. The vaporizer cartridge system of claim 4, wherein the battery assembly comprises a battery cover separable from the battery assembly.

\* \* \* \* \*